United States Patent [19]

Buysch et al.

[11] Patent Number: 5,625,097
[45] Date of Patent: Apr. 29, 1997

[54] PROCESS FOR PREPARING DIPHENYLAMINES AND CATALYSTS USABLE FOR THIS PURPOSE

[75] Inventors: Hans-Josef Buysch, Krefeld; Christine Mendoza-Frohn, Erkrath; Jürgen Scharschmidt, Krefeld; Ulrich Notheis; Rudolf J. Klee, both of Dormagen; Gerhard Darsow, Krefeld, all of Germany

[73] Assignee: Bayer Aktiengesellschaft, Leverkusen, Germany

[21] Appl. No.: 524,556

[22] Filed: Sep. 7, 1995

[30] Foreign Application Priority Data

Sep. 14, 1994 [DE] Germany ............ 44 32 646.7

[51] Int. Cl.$^6$ ............................................. C07C 209/22
[52] U.S. Cl. ............................................. 564/398; 502/326
[58] Field of Search ............................................. 564/398

[56] References Cited

U.S. PATENT DOCUMENTS 4,729,977  3/1988  Immel et al. ............ 502/170
5,196,592  3/1993  Immel et al. ............ 564/415
5,338,885  8/1994  Immel et al. ............ 654/398

FOREIGN PATENT DOCUMENTS 0208933  1/1987  European Pat. Off. .
0494455  7/1992  European Pat. Off. .
0526793  2/1993  European Pat. Off. .
0535484  4/1993  European Pat. Off. .

*Primary Examiner*—Brian M. Burn
*Attorney, Agent, or Firm*—Sprung Horn Kramer & Woods

[57] ABSTRACT

The preparation of optionally substituted diphenylamine by reaction of optionally substituted aniline with optionally substituted cyclohexanone using a supported Rh catalyst containing rhodium or a combination of rhodium with another platinum metal from the group of palladium, platinum, ruthenium or iridium and which can additionally contain chromium, manganese, alkali metal and a sulphur compound is described. The catalyst of the invention is prepared from halide-free starting materials. The Rh catalyst is distinguished by a low dependence of the initial selectivity, the selectivity in the run-in state and the running-in time on the conditions of the reductive pretreatment and requires only short running-in times to the optimum state.

4 Claims, No Drawings

PROCESS FOR PREPARING DIPHENYLAMINES AND CATALYSTS USABLE FOR THIS PURPOSE

BACKGROUND OF THE INVENTION

1. Field of the Invention

The invention relates to the preparation of optionally substituted diphenylamine by reaction of optionally substituted aniline with optionally substituted cyclohexanone using Rh catalysts from halogen-free salts.

2. Description of the Related Art

Supported Rh catalysts for the preparation of optionally substituted diphenylamine by reaction of optionally substituted aniline with optionally substituted cyclohexanones are known, for example, from EP 535 484.

For this purpose, EP 535 484 describes a supported catalyst containing rhodium or a combination of rhodium with another platinum metal from the group of palladium, platinum, ruthenium or iridium. The noble metals are present in a total amount of from 0.05 to 5% by weight, based on the total weight of the catalyst. The catalyst described in EP 535 484 additionally contains from 1 to 12% by weight of alkali metal and optionally from 1 to 12% by weight of sulphur and also optionally from 0.05 to 8% by weight of chromium and manganese, based on the support material.

The Rh catalyst described in EP 535 484 is prepared, after the heat treatment of the catalyst support treated with chromium and manganese, by applying rhodium or rhodium and a further noble metals by known methods. A description is given of the deposition of the rhodium or the rhodium and the further noble metals from the aqueous solution of their salts, with salts such as chloride, nitrate, acetate being mentioned without any differentiation or preference. However, the examples in EP 535 484 are based only on the use of chlorides.

The deposition of the Rh salt and optionally the noble metal salts is carried out by precipitation with basic ammonium or alkali metal compounds in aqueous solution, which basic compounds are applied either before or after the Rh or the noble metals. Independently of the treatment with sulphur compounds, which is optionally carried out in a further preparation step, no washing procedure is finally carried out prior to drying, reductive pretreatment and the use of the catalyst for the preparation of the optionally substituted diphenylamines. The anion of the Rh salt or the noble metal salts, in the example the chloride, thus remains in the catalyst.

In the preparation, for example, of the unsubstituted diphenylamine from aniline and cyclohexanone over the Rh catalysts from the chlorides described in the examples of EP 535 484, a series of byproducts including N-cyclohexylaniline, carbazole, cyclohexanol, phenol and benzene are formed. In addition, the intermediate of the reaction to give diphenylamine, namely N-cyclohexylideneaniline, is obtained.

The amounts of the byproducts and intermediates formed are strongly dependent, according to our own studies, on the pretreatment conditions of the catalyst (reduction temperature and time). EP 535 484 recommends a reduction temperature of from 120° to 400° C. In EP 208 923, in which the catalyst of EP 535 484 is claimed, the reduction temperature specified is even the further range of from 120° to 450° C. and the duration specified is from 30 to 80 hours.

Furthermore, the composition of the product stream of the reaction alters greatly during the running-in of the catalyst. However, although the selectivity for the desired product diphenylamine increases during this time, a considerable amount of byproducts which can mostly no longer be used in the process is obtained depending on the initial selectivity and depending on the required duration of the running-in phase; in particular, benzene interferes as byproduct. Long running-up phases with gradually changing product composition likewise have an adverse effect on the work-up of the product stream. Furthermore, the strong dependence of the product composition on the duration and temperature of the hydrogenative pretreatment of the catalyst places high demands on the exact adherence to these conditions.

It would therefore be desirable to find an Rh catalyst for preparing optionally substituted diphenylamine from optionally substituted aniline and optionally substituted cyclohexanone which avoids the difficulties described: desirable aspects are low sensitivity of the product composition to the type of reductive pretreatment of the catalyst, high initial selectivity and short running-in time of the catalyst into its steady state of maximum selectivity with simultaneously minimal benzene values.

SUMMARY OF THE INVENTION

It has now surprisingly been found that in the preparation of optionally substituted diphenylamine from optionally substituted aniline and optionally substituted cyclohexanone over an Rh catalyst containing rhodium or rhodium and a further platinum metal from the group of platinum, palladium, ruthenium and iridium and optionally containing chromium and manganese, alkali metal and/or sulphur and on which the rhodium, optionally the further noble metals and optionally the chromium and the manganese have been deposited from halogen-free starting materials, a significant shortening of the running-in phase of the Rh catalyst and a far lower sensitivity of the selectivity to the conditions of the pretreatment of the catalyst are obtained. In other words, the invention relates to the fact that the anions of the catalyst active substances described as equally useful in EP 535 484 are in no way equally useful and thus to the fact that the consistent omission of the halide ions effects unforeseeable advantages.

The invention provides a process for preparing diphenylamines of the formula

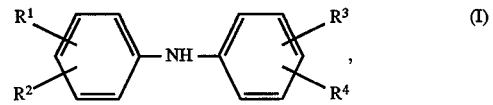

where
$R^1$, $R^2$, $R^3$ and $R^4$ are, independently of one another, hydrogen, $C_1$–$C_4$-alkyl or $C_1$–$C_4$-alkoxy,
by reaction of anilines of the formula

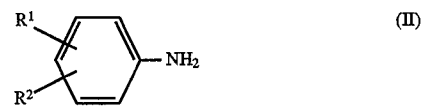

with cyclohexanones of the formula

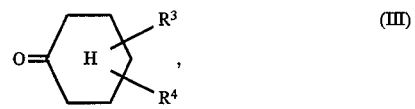

where $R^1$ to $R^4$ are as defined above,
at 200°–450° C. and 0.1–20 bar using a supported catalyst containing from 0.05 to 5% by weight of Rh or a mixture of Rh and one or more noble metals from the group of Pt, Pd, Ru and Ir, where in the case of a mixture Rh makes up from 10 to 90% of the weight of the mixture, and where the catalyst can further contain from 0.05 to 8% by weight of Cr and Mn in a weight ratio Cr:Mn=5:1 to 1:5, from 0.05 to 15% by weight of alkali metal and from 0.05 to 6% by weight of sulphur, where all figures are calculated as metal or elemental sulphur and are based on the total weight of the catalyst, characterized in that the supports used for preparing the catalyst and the compounds of the noble metals, the Cr, Mn, the alkali metals and the S used are halogen-free.

DETAILED DESCRIPTION OF THE INVENTION $C_1$–$C_4$-Alkyl or $C_1$–$C_4$-alkoxy in the substituents $R^1$–$R^4$ are, for example, methyl, ethyl, propyl, isopropyl, butyl, isobutyl, methoxy, ethoxy, propoxy, isopropoxy, butoxy or isobutoxy. The specified substituents preferably have 1–2 carbon atoms, they are particularly preferably methyl or methoxy. Further preference is given to the substituent $R^2$ or $R^4$ being hydrogen, while the substituents $R^1$ and $R^3$ assume the specified scope of meanings. Particularly preferably, the process is directed at the preparation of unsubstituted diphenylamine.

Cyclohexanone can also be used in a mixture with phenol, for example, if it was prepared from phenol by hydrogenation.

The starting compounds aniline and cyclohexanone or aniline and cyclohexanone/phenol mixture are used in a molar ratio of from 1:10 to 10:3, preferably from 1:2 to 2:1. The starting compounds are vaporized individually or together and the vapour mixture formed is, optionally by means of a carrier gas stream, brought over the above-described rhodium-containing catalyst. Carrier gases for this purpose are, for example, nitrogen, hydrogen, argon, lower hydrocarbons such as methane, ethane or natural gas and also mixtures thereof. Preferably, nitrogen or hydrogen or a mixture thereof is used as carrier gas. The carrier gas is used in an amount of from 1. to 100 1/g of starting material, preferably from 1 to 50 1/g of starting material. The weight hourly space velocity over the catalyst is set at from 0.01 to 1/kg of starting material per 1/catalyst and hour.

Apart from the specified starting compounds aniline and cyclohexanone and the partial replacement of the cyclohexanone by the corresponding phenol already described, it is possible to use further materials such as N-cyclohexylideneaniline or dicyclohexylamine or N-cyclohexylaniline.

The process of the invention is carded out at a temperature of from 200° to 450° C., preferably 200°–400° C., and a pressure of from 0.1 to 20 bar, preferably from 1 to 6 bar, in the gas phase. The combination of reaction temperature and reaction pressure are selected in a manner known to those skilled in the art in such a way that the reaction can always be carried out in the gas phase.

The invention further provides the specified halogen-free, Rh-containing catalyst.

Catalyst supports for the Rh catalysts of the invention are the customary ones, in particular α- and γ-aluminium oxide, aluminium spinels, silica gel, kieselguhr, montmorillonites, pumice and/or activated carbon.

The catalyst of the invention contains rhodium or a combination of rhodium with another platinum metal from the group of palladium, platinum, ruthenium or iridium. The noble metals are present in a total amount of from 0.05 to 5% by weight, preferably from 0.05 to 4% by weight, particularly preferably from 0.1 to 3% by weight, based on the total weight of the catalyst.

The catalyst to be used according to the invention preferably contains such a combination of rhodium with at least one of the other platinum metals specified in which rhodium is present in an amount of from 10 to 90% of the total weight of all noble metals. Particularly preferably, rhodium is combined with palladium or platinum or a mixture of palladium and platinum. Very particularly preferably, the rhodium is combined with palladium and platinum alone. In such a combination, the proportion of the rhodium is from 10 to 90%, preferably from 15 to 80%, particularly preferably from 20 to 70%, of the total weight of all noble metals.

The rhodium or the rhodium and the further noble metals are applied by known methods, e.g. by impregnation of the catalyst support with the corresponding noble metal salt solutions. According to the invention, suitable salts are halogen-free noble metal salts such as nitrates, acetates, sulphates, oxalates, $H_3[Rh(SO_4)_3]$, preferably nitrates. Further preference is given to applying Rh in the form of $H_3[Rh(SO_4)_3]$. Preferably, the noble metal salts are, after impregnation of the catalyst, decomposed in a stream of air and/or nitrogen for from 2 to 48 hours at from 200° to 500° C. The Rh salt and optionally the further noble metal salts can also be precipitated on the support in a known manner by precipitation with alkali hydroxide solution. It is here possible in principle to first impregnate the support with basic ammonium or alkali metal compounds in aqueous solution, to dry it and then to apply the individual noble metal salt solutions together or separately or, the other way around, first to carry out the joint or separate noble metal impregnation, to dry the material and then to treat it subsequently with alkali hydroxide solution. The catalyst of the invention contains 0.01–6 % by weight of alkali hydroxide solution, preferably 0.05–5 % by weight, based on the total weight of the catalyst.

Suitable alkali solutions for the alkali treatment are, for example, aqueous solutions of inorganic and/or organic alkali compounds such as the oxides, hydroxides and/or alkoxides of the alkali metals and also the salts of those acids which neither themselves nor in the form of their reaction products count as hydrogenation catalyst poisons in the context of the customary formulation (e.g. according to Zymalkowski: "Katalytische Hydrierung", (1965), page 36; Houben-Weyl (1955), Volume 4/2, page 257), thus particularly those which are free of N, P, As, Sb, Se, Te, Cl, Br and I, such as the carbonates, bicarbonates, acetetes and/or the salts of other lower carboxylic acids. Examples of alkali compounds which may be mentioned are: lithium hydroxide, sodium hydroxide, sodium carbonate, sodium hydrogen carbonate, sodium methoxide, sodium ethoxide, sodium acetate, potassium hydroxide, potassium carbonate, potassium methoxide and/or rubinium hydroxide. The concentration of the alkali compounds in the alkali solution used is generally from about 0.02 to 5N, preferably from 0.02 to 2N, in particular from 0.01 to 1N.

Sulphur compounds can additionally be applied to the catalyst of the invention. Examples of suitable sulphur compounds which may be mentioned are: the sulphates, sulphites, thiosulphates and thiocyanates of the alkali metals, preferably $K_2SO_4$, $Na_2SO_4$, $Na_2SO_3$, $Na_2S_2O_3$, KSCN and NaSCN. These salts can be used either individually or in admixture with one another. However, they can also be dissolved in water together with the alkali compounds and thus be applied in admixture to the supported catalyst.

To apply the sulphur-containing compounds onto the catalyst, the salts specified are dissolved in water and the catalyst already containing the noble metals is impregnated or sprayed with this solution.

The specified sulphur compounds are present in the catalyst at a content of 0.05–6% by weight, preferably up to 0.05–5% by weight (based on the catalyst weight).

If, in place of the untreated support materials, supports treated in a known manner with chromium and manganese are used for the preparation of the catalyst of the invention, the Rh catalyst can additionally contain from 0.05 to 8% by weight of chromium and manganese together, preferably from 0.2 to 5% by weight, based on the catalyst weight. The weight ratio of the elements chromium and manganese in the supported catalyst of the invention is from about 5:1 to 1:5, preferably from 10:9 to 1:2.

The chromium and manganese can be applied to the catalyst support, for example, by joint precipitation of a manganese-chromium hydroxide mixture from a chromium and manganese salt solution using alkali hydroxide solution or ammonia and subsequently washing out the soluble components with water. Suitable chromium and manganese salts are likewise halogen-free salts, in particular the sulphates, acetates and/or nitrates of the elements specified. The deposition of the chromium and manganese onto the catalyst support can also be carried out as ammonium manganese chromate or ammonium alkali metal manganese chromate from a solution of manganese(II) salts and ammonium dichromate by means of ammonia and/or basic alkali compounds. Particularly uniform and strongly adhering deposits are obtained if the addition of base is carried out slowly and uniformly, avoiding relatively large concentration differences. In a preferred embodiment, the precipitation is therefore carried out by means of urea under hydrolyzing conditions, whereby the abovementioned conditions are ensured particularly well.

After the application of the chromium and manganese compounds onto the catalyst support, the catalyst support thus treated is washed free of sulphate before being heated to relatively high temperatures (from about 200° to 450° C., preferably from 250° to 350° C). The catalyst support treated with chromium and manganese compounds is heat treated for from about 0.5 to 3 hours, preferably from 1 to 2 hours.

After the last preparative step, the catalyst of the invention can be used directly for a dehydrogenation reaction; but it is more advantageous to treat it with hydrogen at 200°–450° C. for 4–80 hours prior to use. The hydrogen is preferably diluted with inert gas. The pretreating reduction is preferably carried out in the reactor in which the preparation of the optionally substituted diphenylamines also takes place.

Diphenylamines are precursors for rubber auxiliaries and phenothiazine dyes and can be directly used as preservatives for citrus fruits.

Examples of Catalyst Preparation

Comparative Example for Catalyst Preparation

As described in EP 208 933 (Examples 1a and 5), 100 g of spherical $\gamma$-$Al_2O_3$ (diameter: from 2 to 5 mm) having a specific surface area of 350 m$^2$/g were initially charged in a round-bottomed flask and admixed with a solution of 3.8 g of $MnSO_4H_2O$, 2.8 g of $(NH_4)_2Cr_2O_7$ and 22 g of urea in 72 ml of water. The flask was maintained at 85° C. for one hour while being rotated, the liquid not absorbed was filtered off and the catalyst support was washed free of sulphate and then dried for 25 hours at 110° C. under a waterpump vacuum. The catalyst support thus treated was subsequently heat treated at 330° C. for 30 minutes. The catalyst support thus treated with chromium and manganese was then uniformly impregnated in a round-bottomed flask with a solution of 2.03 g of rhodium trichloride in 30 ml of water. The moist catalyst pellets were dried at 100° C. in a waterpump vacuum and then again impregnated with a solution of 2.92 g of sodium hydroxide and 2.92 g of $K_2SO_4$ in 30 ml of water. The catalyst pellets were then dried for 43 hours at 100° C. in a waterpump vacuum.

EXAMPLE 1

The catalyst preparation was carried out as in the comparative example. However, the catalyst support treated with chromium and manganese was impregnated with a solution of 2.8 g of $Rh(NO_3)_3$ in 30 ml of water rather than with a solution of rhodium trichloride, dried at 100° C. in a waterpump vacuum and heat treated for 3 hours at 300° C. in air. The further treatment with alkali and sulphur compound and the final drying were carried out as in the comparative example.

EXAMPLE 2

The catalyst preparation corresponds to that in Example 1, but it was carried out on an unpretreated support without chromium and manganese: 100 g of spherical $\gamma$-$Al_2O_3$ (diameter from 2 to 5 mm) having a specific surface area of about 300 m$^2$/g were impregnated with a solution of 2.8 g of $Rh(NO_3)_3$ in 30 ml of water, dried at 100° C. in a waterpump vacuum and heat treated for 3 hours at 300° C. in air. The pellets were then again impregnated with a solution of 2.92 g of NaOH and 2.92 g of $K_2SO_4$ in 30 ml of water and finally dried at 100° C. for 48 hours in a waterpump vacuum.

EXAMPLE 3

The catalyst preparation was carried out as in the comparative example on a support treated with chromium and manganese. However, the impregnation solution was 3.83 g of $H_3[Kh(SO_4)_3]$ in 30 ml of water and the catalyst was dried at up to 100° C. in a waterpump vacuum. Subsequently, it was again impregnated with 2.92 g of sodium hydroxide in 30 ml of water. The catalyst pellets were then dried for 48 hours at 100° C. in a waterpump vacuum.

EXAMPLE 4

The catalyst preparation was carried out on the support treated with chromium and manganese as in the comparative example. 1.4 g of $Rh(NO_3)_3$ and 0.76 g of $Pt(NH_3)_4(OH)_2$ were dissolved in 30 ml of water and the impregnation was carried out using this solution. After drying at 100° C. in a waterpump vacuum, heat treatment was carried out for 4 hours in air at up to 300° C. The further alkali treatment and the final drying were carried out as in the comparative example. (See Table 5).

Examples of Catalyst Use

Prior to using the catalysts for preparing diphenylamine, they were pretreated by reduction in a mixture of 10% by volume of $H_2$ and 90% by volume of $N_2$. The reduction temperature and duration are in each case given in the examples.

For the activity studies, 6 ml of the rhodium-containing supported catalyst was in each case heated to the desired reaction temperature (350° C.) in a vertically arranged, electrically heatable glass tube having a length of about 70 cm and an internal diameter of 17 mm. The starting material, a mixture of aniline and cyclohexanone in a molar ratio of 2.5:1, was fed into the reaction tube at the top by means of a perfusion pump (2.4 g/h). The upper part of the tube contained column packing which aided the vaporization of the liquid starting material prior to contact with the catalyst.

EXAMPLE 5 (FOR COMPARISON)

Separate samples of the catalyst from the comparative example were reduced at 250°, 325°, 375° and 425° C.

respectively for 24 hours in a mixture of 10% by volume of $H_2$ and 90% by volume of $N_2$. Table 1 gives the results of the activity studies.

EXAMPLE 6

Separate samples of the catalyst from Example 1 were reduced at 250°, 325°, 375° and 425° C. respectively for 24 hours in a mixture of 10% by volume of $H_2$ and 90% by volume of $N_2$. For the result, see Table 2.

EXAMPLE 7

Separate samples of the catalyst from Example 2 were reduced at 250°, 325°, 375° and 425° C. respectively for 24 hours in a mixture of 10% by volume of $H_2$ and 90% by volume of $N_2$. For the result, see Table 3.

EXAMPLE 8

Separate samples of the catalyst from Example 3 were reduced at 250°, 325°, 375° and 425° C. respectively for 24 hours in a mixture of 10% by volume of $H_2$ and 90% by volume of $N_2$. For the result, see Table 4.

EXAMPLE 9

Separate samples of the catalyst from Example 4 were reduced at 250° and 425° C. respectively for 24 hours in 10% $H_2$/90% $N_2$.

For the result, see Table 5.

TABLE 1

Comparative catalyst/Example 5

| | | | | in the steady state | | | | | |
|---|---|---|---|---|---|---|---|---|---|
| Reduction of the catalyst (°C.) | Diphenyl- amine, initial (%) | Benzene, initial (%) | Running-in time (h) | Diphenyl- amine (%) | Cyclo- hexanone (%) | N-Cyclo- hexylidene- aniline (%) | N-Cyclo- hexyl- aniline (%) | Benzene (%) | Aniline (%) |
| 250 | 11.9 | 15.3 | 230 | 29.1 | 1.4 | 3.2 | 1.5 | 0.9 | 62.7 |
| 325 | 18.2 | 11.5 | 200 | 29.3 | 1.8 | 2.6 | 0.9 | 0.9 | 63.0 |
| 375 | 14.4 | 8.6 | 180 | 26.5 | 4.4 | 2.4 | 1.1 | 0.8 | 63.8 |
| 425 | 16.9 | 9.7 | 160 | 25.6 | 3.9 | 4.1 | 1.0 | 0.8 | 63.4 |

Figures in % by weight of the product stream
N-Cyclohexylideneaniline, N-cyclohexylaniline = recyclable intermediates, remainder = non-recyclable byproducts

TABLE 2

Catalyst from Example 1/Example 6

| | | | | in the steady state | | | | | |
|---|---|---|---|---|---|---|---|---|---|
| Reduction of the catalyst (°C.) | Diphenyl- amine, initial (%) | Benzene, initial (%) | Running-in time (h) | Diphenyl- amine (%) | Cyclo- hexanone (%) | N-Cyclo- hexylidene- aniline (%) | N-Cyclo- hexyl- aniline (%) | Benzene (%) | Aniline (%) |
| 250 | 15.5 | 4.6 | 150 | 30.9 | 3.3 | 3.9 | 2.2 | 0.6 | 55.2 |
| 325 | 15.4 | 3.5 | 130 | 25.5 | 4.2 | 4.4 | 1.9 | 0.5 | 57.6 |
| 375 | 21.1 | 2.0 | 130 | 29.7 | 2.9 | 2.8 | 1.6 | 0.5 | 56.3 |
| 425 | 18.4 | 2.2 | 130 | 35.7 | 3.2 | 3.4 | 2.0 | 0.6 | 52.5 |

Figures in % by weight of the product stream
N-Cyclohexylideneaniline, N-cyclohexylaniline = recyclable intermediates, remainder = non-recyclable byproducts

TABLE 3

Catalyst from Example 2/Example 7

| | | | | in the steady state | | | | | |
|---|---|---|---|---|---|---|---|---|---|
| Reduction of the catalyst (°C.) | Diphenyl- amine, initial (%) | Benzene, initial (%) | Running-in time (h) | Diphenyl- amine (%) | Cyclo- hexanone (%) | N-Cyclo- hexylidene- aniline (%) | N-Cyclo- hexyl- aniline (%) | Benzene (%) | Aniline (%) |
| 250 | 22.8 | 3.0 | 150 | 34.1 | 3.2 | 3.5 | 0.3 | 0.8 | 54.9 |
| 325 | 25.2 | 2.7 | 140 | 31.4 | 2.8 | 4.7 | 1.7 | 0.7 | 55.3 |
| 375 | 25.0 | 2.9 | 130 | 28.0 | 3.9 | 6.4 | 1.6 | 0.6 | 56.1 |
| 425 | 21.4 | 2.4 | 130 | 34.0 | 1.7 | 5.2 | 0.9 | 0.6 | 54.3 |

Figures in % by weight of the product stream
N-Cyclohexylideneaniline, N-cyclohexylaniline = recyclable intermediates, remainder = non-recyclable byproducts

TABLE 4

| | | | | Catalyst from Example 3 | | | | | |
|---|---|---|---|---|---|---|---|---|---|
| | | | | | in the steady state | | | | |
| Reduction of the catalyst (°C.) | Diphenyl-amine, initial (%) | Benzene, initial (%) | Running-in time (h) | Diphenyl-amine (%) | Cyclo-hexanone (%) | N-Cyclo-hexylidene-aniline (%) | N-Cyclo-hexyl-aniline (%) | Benzene (%) | Aniline (%) |
| 250 | 21.7 | 6.1 | 160 | 34.3 | 3.1 | 3.5 | 0.9 | 1.1 | 54.1 |
| 325 | 21.9 | 6.8 | 120 | 37.2 | 1.9 | 3.3 | 0.6 | 0.9 | 53.0 |
| 375 | 24.2 | 6.1 | 150 | 32.2 | 4.8 | 2.3 | 1.8 | 0.8 | 55.0 |
| 425 | 22.1 | 6.9 | 100 | 32.0 | 4.3 | 3.8 | 1.4 | 0.8 | 54.7 |

Figures in % by weight of the product stream
N-Cyclohexylideneaniline, N-cyclohexylaniline = recyclable intermediates, remainder = non-recyclable byproducts

TABLE 5

| | | | | Catalyst from Example 4 | | | | | |
|---|---|---|---|---|---|---|---|---|---|
| | | | | | in the steady state | | | | |
| Reduction of the catalyst (°C.) | Diphenyl-amine, initial (%) | Benzene, initial (%) | Running-in time (h) | Diphenyl-amine (%) | Cyclo-hexanone (%) | N-Cyclo-hexylidene-aniline (%) | N-Cyclo-hexyl-aniline (%) | Benzene (%) | Aniline (%) |
| 250 | 25.1 | 3.5 | 120 | 27.5 | 3.6 | 6.1 | 0.9 | 1.0 | 56.0 |
| 425 | 25.8 | 1.3 | 80 | 29.5 | 3.7 | 3.5 | 1.4 | 0.5 | 56.3 |

Figures in % by weight of the product stream
N-Cyclohexylideneaniline, N-cyclohexylaniline = recyclable intermediates
Remainder = non-recyclable by products The comparative catalyst from rhodium chloride in Example 5 (Table 1) shows a strong dependence of the initial selectivity and the initial benzene values on the pretreatment of the catalyst a strong dependence of the running-in time on the pretreatment of the catalyst long running-in times.

In contrast, the catalysts prepared from halogen-free salts in the Examples 6 to 9 have, in comparison with Example 5, a far lower sensitivity of the initial selectivity the initial benzene value and the running-in time to the manner of the reductive pretreatment.

In addition, very short running-in times are necessary to bring the catalysts from their in any case good initial selectivities and low benzene values to the run-in state of optimum selectivity.

What is claimed is:

1. A process for preparing a diphenylamine of the formula

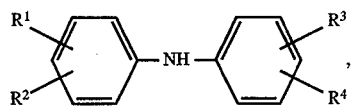

where $R^1$, $R^2$, $R^3$ and $R^4$ are, independently of one another, hydrogen, $C_1$-C-alkyl or $C_1$-$C_4$-alkoxy, by reaction of an aniline of the formula

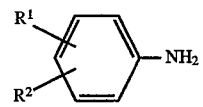

with a cyclohexanone of the formula

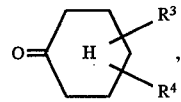

where $R^1$ to $R^4$ are as defined above, at 200°–450° C. and 0.1–20 bar using a supported catalyst containing from 0.05 to 5% by weight of Rh or a mixture of Rh and one or more noble metals from the group consisting of Pt, Pd, Ru and Ir, where in the case of a mixture Rh makes up from 10 to 90% of the weight of the mixture, and where the catalyst can further contain from 0.05 to 8% by weight of Cr and Mn in a weight ratio Cr:Mn=5:1 to 1:5, from 0.05 to 15% by weight of alkali metal and from 0.05 to 6% by weight of sulphur, where all figures are calculated as metal or elemental sulphur and are based on the total weight of the catalyst, wherein the support used for preparing the catalyst and the compounds of the noble metals, the Cr, Mn, the alkali metals and the S used are halogen-free.

2. The process according to claim 1, wherein the supported catalyst has the rhodium on the additional optional noble metals deposited by using nitrates.

3. The process according to claim 2, wherein the supported catalyst has been decomposed for 2 to 48 hours at 200° to 500° C. in air, nitrogen or an air/nitrogen mixture after the nitrates have been deposited on the catalyst support.

4. The process according to claim 1, wherein the support catalyst has the rhodium deposited by using $[H_3[Rh(SO_4)_3]]$.

* * * * *